United States Patent
Gabl et al.

(10) Patent No.: US 7,379,766 B2
(45) Date of Patent: May 27, 2008

(54) CMOS-PROCESS COMPATIBLE HIGH-DC SURFACE COATING FOR CAPACITIVE DETECTION AND STIMULATION OF BIOLOGICAL TISSUES

(75) Inventors: Reinhard Gabl, Munich (DE); Tamara Birkenmaier, Munich (DE); Bjorn-Oliver Eversmann, Munich (DE); Peter Fromherz, Munich (DE); Martin Jenkner, Planegg (DE); Matthias Schreiter, Munich (DE); Roland Thewes, Grobenzell (DE); Wolfram Wersing, Bergen (DE)

(73) Assignee: Infineon Technologies AG, Neubiberg (DE)

( * ) Notice: Subject to any disclaimer, the term of this patent is extended or adjusted under 35 U.S.C. 154(b) by 603 days.

(21) Appl. No.: 10/931,482

(22) Filed: Sep. 1, 2004

(65) Prior Publication Data

US 2005/0187454 A1 Aug. 25, 2005

Related U.S. Application Data

(63) Continuation of application No. PCT/EP03/01871, filed on Feb. 24, 2003.

(30) Foreign Application Priority Data

Mar. 1, 2002 (DE) ................................ 102 09 075

(51) Int. Cl.
*A61B 5/04* (2006.01)
*H01L 21/16* (2006.01)

(52) U.S. Cl. ....................... 600/372; 600/395; 607/115; 438/104

(58) Field of Classification Search ................. 600/372, 600/395; 607/115
See application file for complete search history.

(56) References Cited

U.S. PATENT DOCUMENTS 3,882,846 A * 5/1975 Fletcher et al. ............. 600/395

FOREIGN PATENT DOCUMENTS

| DE | 100 32 568 A1 | 1/2002 |
|----|---|---|
| WO | WO-01/70002 A2 | 9/2001 |

OTHER PUBLICATIONS

Richard Schatzthauer et al.; "Neuron-silicon junction with voltage-gated ionic currents"; European Journal of Neuroscience, vol. 10, No. 6, Jun. 1998, pp. 1956-1962, XP008006938.
S. Vassanelli et al.; "Transistor records of excitable neurons from rat brain"; Applied Physics A: Materials Science and Processing, Springer-Verlag, Berlin, Germany, vol. 66, 1998, pp. 459-463, XP002210066.

(Continued)

Primary Examiner—Lee S Cohen
(74) Attorney, Agent, or Firm—Dickstein Shapiro LLP

(57) ABSTRACT

Biochip for capacitive stimulation and/or detection of biological tissues. The biochip has a carrier structure, at least one stimulation and/or sensor device, which is arranged in or at the carrier structure, and at least one dielectric layer, one layer area of which is arranged at the stimulation and/or sensor device and the opposite layer area of which forms a stimulation and/or sensor area for capacitive simulation and/or detection of biological tissues, wherein the dielectric layer comprises $TiO_2$.

14 Claims, 3 Drawing Sheets

OTHER PUBLICATIONS

S. Vassanelli et al.; "Neurons from rat brain coupled to transistors"; Applied Physics A, Materials & Science Processing, Springer-Verglag, Berlin, Germany, vol. 65, 1997, pp. 85-88, XP002210054.

Bernhard Straub et al.; "Recombinant maxi-K channels on transistor, a prototype of iono-electronic interfacing"; Nature Biotechnology, Nature Publishing, US., vol. 19, No. 2, Feb. 2001, pp. 121-124, XP002210053.

Peter Fromherz et al.; "A Neuron-Silicon Junction: A Retzius Cell of the Leech on an Insulated-Gate Field-Effect Transistor"; American Association for the Advancement of Science, US., vol. 252, May 31, 1991, pp. 1290-1293, XP000574048.

Alfred Stett et al.; "Two-way silicon-neuron interface by electrical induction"; Physical Review E, Statistical Physics, Plasmas, Fluids, and Related Interdisciplinary Topics, American Institute of Physics, New York, NY, US, vol. 55, No. 2, Feb. 1997, pp. 1779-1782, XP000913528.

Stefano Vassanelli et al.; "Transistor Probes Local Potassium Conductances in the Adhesion Region of Cultured Rat Hippocampal Neurons"; The Journal of Neuroscience, Aug. 15, 1999, vol. 19, No. 16, pp. 6767-6773, XP008006937.

Peter Fromherz; "Interfacing Neurons and Silicon by Electrical Induction"; Berichte Der Bunsen-Gesellschaft Fur Physikalische Chemie, Verlag Chemie, Weinheim, Germany, vol. 100, No. 7, 1996, pp. 1093-1102, XP000907082.

* cited by examiner

US 7,379,766 B2

CMOS-PROCESS COMPATIBLE HIGH-DC SURFACE COATING FOR CAPACITIVE DETECTION AND STIMULATION OF BIOLOGICAL TISSUES

CROSS-REFERENCE TO RELATED APPLICATION

This application is a continuation of International Patent Application Ser. No. PCT/EP03/01871, filed Feb. 24, 2003, which published in German on Sep. 12, 2003 as WO 03/074683, and is incorporated herein by reference in its entirety.

FIELD OF THE INVENTION

The invention relates to a biochip for capacitive stimulation and/or detection of biological tissues and to a method for producing a corresponding biochip.

BACKGROUND OF THE INVENTION

On the laboratory scale, it has already been a good ten years since direct communication between nerve cells and electrically active solid-state structures, such as e.g. semiconductors, left the realm of fiction. Successful laboratory experiments have been reported for example by P. Fromherz et al. in Science 252, 1290 (1991); P. Fromherz et al. in Physical Review Letters 75, 1670 (1995) and also P. Stett et al. in Physical Review E Vol. 55, No. 2, 1779 (1997). A summary overview of the early results is given by P. Fromherz in Berichte der Bunsen Gesellschaft No. 7, 1093 (1996). Furthermore, first biochips produced on industrial scales have recently been presented. Modern biochips are thus opening up a wide variety of fields of use from neurobiological fundamental research through to high-throughput screening applications in the pharmaceutical industry.

A basic element of such modern biochips is illustrated schematically in FIG. 5(a). The biochip comprises a carrier structure 10, which may comprise for example a patterned semiconductor substrate (semiconductor structure). The carrier structure 10 is separated from an electrolyte 14 by a dielectric layer 12. The corresponding equivalent circuit diagram is illustrated in FIG. 5(b). Generally, in an electrolyte, the electrically communicating nerve cells are cultivated directly at those locations on the surface of the carrier structure 10 where the active locations of electrical stimulation and detection devices are situated.

Whereas the electrical activity is carried by ions in biological systems, electrons or holes are responsible for charge transport in semiconductors. Therefore, in a manner corresponding to the natural boundary layer between electrolyte 14 and semiconductor structure, a capacitive coupling is preferably utilized both during the stimulation and during the detection of biological processes. This currentless mechanism of electrical coupling between the biochip and the nerve cell to be stimulated or to be detected is based on the principle of electrical induction (electrostatic induction, also called influence). The electrical coupling is brought about by the fact that an accumulation of charge in the nerve cell induces corresponding mirror charges in the biochip, the effect of which for example on the electrical transport properties of the carrier structure 10 designed as a semiconductor structure can be demonstrated.

Conversely, nerve cells arranged at the dielectric layer 12 of the carrier or semiconductor structure 10 can be stimulated by virtue of the fact that an accumulation of charge in a stimulation device of the semiconductor structure 10 induces charges in the nerve cell. The dielectric layer 12 between the semiconductor structure 10 and the electrolyte 14 is accorded a particular importance in the case of such a biochip which utilizes a capacitive coupling to the nerve cell to be examined both during stimulation processes and during detection processes.

Conventionally, silicon-based, active and thus CMOS-enabled semiconductor structures are coated with $SiO_2$ in order to form such a dielectric boundary or surface layer 12. It has been shown, however, that, in particular with regard to the coupling efficiency or the achievable signal transfer between stimulation and/or sensor device of the biochip and the biological tissues being examined, a dielectric layer made of $SiO_2$ yields results that are satisfactory only to a limited extent.

SUMMARY OF THE INVENTION

Accordingly, it is an object of the invention to provide a biochip which enables an improved coupling efficiency or an enhanced signal transfer between stimulation and/or detection devices of the biochip and the biological tissues to be examined. Furthermore, it is an object of the invention to specify a method for producing a corresponding biochip.

According to the invention, a biochip for capacitive stimulation and/or detection of biological tissues comprises
   a carrier structure;
      at least one stimulation and/or sensor device, which is arranged in or at the carrier structure;
      at least one dielectric layer, one layer area of which is arranged at the stimulation and/or sensor device and the opposite layer of which forms a stimulation and/or sensor area for capacitive simulation and/or detection of biological tissues;
   the dielectric layer comprising $TiO_2$.

According to the invention, the dielectric layer, which is arranged operationally between the carrier structure of the biochip and an electrolyte with the biological material to be examined, comprises $TiO_2$, the dielectric layer preferably essentially consisting of $TiO_2$. The carrier structure may be produced from a carrier substrate for example by means of planar-lithographic process steps as are known in particular from CMOS semiconductor technology. The stimulation and/or sensor devices are preferably formed by means of a CMOS process in a silicon semiconductor substrate.

It has surprisingly been shown that a dielectric layer comprising $TiO_2$ has significant advantages in comparison with conventional dielectric boundary layers made of $SiO_2$. In particular, a dielectric layer having $TiO_2$, in comparison with an $SiO_2$ boundary layer, leads to a significantly improved coupling efficiency or to a higher signal transfer between biochip and biological material. The following advantages of a biochip according to the invention having a dielectric boundary layer having $TiO_2$ may be especially highlighted:

(a) High Specific Capacitance

On the basis of the relationship $$c = \frac{\varepsilon_r \varepsilon_0}{d},$$

where c is the specified capacitance of the "boundary layer capacitor" in $F/m^2$, $\epsilon_0 = 8.85 \times 10^{-12}$ As/Vm is the electric constant, $\epsilon_r$ is the dielectric constant (also called relative permittivity) and d is the thickness of the dielectric layer in meters, the layer, for a high specific capacitance, should on the one hand be as thin as possible and on the other hand be composed of a material having a high dielectric constant. The entire layer should also have such a high dielectric constant even in the case of small layer thicknesses and in contact with different materials.

Dielectric constants of 46 were able to demonstrated experimentally in the case of biochips according to the invention which have $TiO_2$ layers as dielectric boundary layers. Such dielectric constants are distinctly above those of $SiO_2$, $Si_3Ni_4$, $Al_2O_3$, $ZrO_2$, $HfO_2$, $La_2O_3$, $Ta_2O5$ and $Y_0O_3$. Since the specific capacitance of the carrier structure/electrolyte interface, which is dominated by the dielectric coating of the carrier structure, for example a semiconductor structure, is a significant parameter in optimizing the coupling efficiency or the signal transfer, a significant improvement in comparison with dielectric boundary layers that are conventionally used can be achieved through the choice of $TiO_2$.

(b) Leakage Conductivity

The dielectric boundary layer of a biochip according to the invention has a very low leakage conductivity, thereby precluding electrolytic reactions at the layer surface which are accompanied by ohmic currents.

(c) Stability and Corrosion

In contrast to conventional capacitors, which are delimited by a solid contact on both sides, the "capacitor construction" of a biochip has to withstand a single-sided contact connection by an aqueous solution with dissolved ions. In particular, the properties of the dielectric boundary layer ought not to change even with application of an electrical voltage. Furthermore, metabolic products of the biological material, for example of a cell culture, should not lead to a chemical corrosion of the dielectric interface. It has surprisingly been established that dielectric boundary layers having $TiO_2$—in contrast to $Si_3N_4$ layers—have a high stability and little tendency toward corrosion.

(d) Biocompatibility

Conversely, the dielectric boundary layer, in particular under electrical voltage, also must not release particles into the electrolyte either by dissolution or by corrosion. Since the interactions between the dielectric boundary layer and the biological tissues are of complex nature, ultimately only the vitality of cells on the layer surface is a measure of the biocompatibility of the applied biological material. Vitality is understood to be, in particular, the sustainment of the growth capability that enables the formation of neurites on the surface.

Surprisingly, a dielectric layer having $TiO_2$ also satisfies this requirement in an outstanding manner. Thus, a growth of cell structures on $TiO_2$ layers was able to be successfully demonstrated. Dielectric layers having $TiO_2$ are thus superior to surface coatings which contain poisonous heavy metals or other toxic substances (such as PZT, for example, which contains lead).

(e) Surface Constitution

It has been shown that a dielectric layer having $TiO_2$ furthermore has a particularly advantageous surface constitution. Thus, the growth capability of cells is influenced not only by the composition of the boundary layer but also, in particular, by the topology of the surface on which the cells are cultivated. Preferably, the surface has an only weakly pronounced topology. In particular, the dimensions of the characteristic quantities of the surface structure should be several orders of magnitude less than those which are used in order for example to cause a directed cell growth. For typical cells, the surface structures should thus be smaller than 10 nm. Such plane surfaces additionally keep open the possibility of micromechanical or photolithographic patterning.

These properties are satisfied by a dielectric layer having $TiO_2$ in an outstanding manner. Furthermore, it was possible to show that the growth of a cell culture has no appreciable effects on the surface structure of such a dielectric layer. Both before and after the growth of the cell culture, the height fluctuations of the dielectric surface were only a few nanometers, so that the boundary surface can be classified as smooth.

(f) Cleaning Capability

It has been shown that such smooth dielectric layers having $TiO_2$ additionally afford the advantage of a straightforward cleaning capability. Preferably, surfaces for the growth of cell cultures should not only be smooth but also be completely accessible to cleaning solutions and readily rinsable. The dielectric layer of a biochip according to the invention is resistant in a wide pH range, so that it possible to use customary cleaning solutions for biological materials which in some instances have extreme pH values.

The cleaning capability of surfaces furthermore also includes the sterilizability thereof. Planar systems especially suit UV sterilization, which, however, presupposes a corresponding UV stability. It is advantageous that the UV stability of dielectric layers having $TiO_2$ is so pronounced that biochips according to the invention can be subjected to a sterilization treatment by UV irradiation prior to an operational use. The UV durability of $TiO_2$ layers thus constitutes an important advantage over most organic surface coatings.

(g) Homogeneity

Furthermore, it was possible to show that dielectric layers having $TiO_2$ can be produced with sufficient homogeneity. This is because the above-described requirements made of the dielectric layer should preferably be fulfilled for the entire stimulation and/or sensor area. Even small regions with high layer conductivity suffice, for example, to destroy the desired insulator character of the entire layer. The same similarly holds true for a distribution of the dielectric constants or for the layer thickness.

(h) CMOS Integrability

A particular advantage of dielectric boundary layers having $TiO_2$ is their CMOS integrability. The position of the dielectric layer in the topmost and thus last processed layer of a CMOS process has the effect that in the course of its deposition, consideration must be given to the structures that may be present. This restricts in particular the temperature range of the deposition process used and also the duration of the process step. The deposition process for the dielectric layer thus has to be matched to the "thermal budget" of the biochip in the back end process stage. Preferably, a maximum temperature of approximately 500° C. should not be exceeded.

Surprisingly, it has been shown that $TiO_2$ layers can be deposited at temperatures of around 400° C. for example by means of reactive RF sputtering, with a quality which satisfies all the above properties. Such a reactive RF sputtering process can also be used as a back end process in a CMOS production method. A sputtering method using pulsed DC sources may also be used.

$TiO_2$ layers furthermore have the advantage that their production also does not disadvantageously alter in some other way the structures that have already been processed below the surface layer.

Furthermore, the TiO$_2$ layers can be produced by means of industrially customary methods on semiconductor wafers of customary size.

A further advantage of a dielectric layer having TiO$_2$ resides in its high mechanical strength. Thus, it was possible to demonstrate that, in contrast to Al$_2$O$_3$, in the course of preparing the dielectric interface of a biochip according to the invention for an experimental use, applied dielectric layer was not damaged or abraded.

Preferably, the stimulation device comprising a metal electrode, the electrical potential of which can be controlled externally, and the dielectric layer being arranged at the metal electrode.

Preferably, the carrier structure comprises a semiconductor structure. The semiconductor structure may be, in particular, a silicon CMOS structure.

Preferably, the sensor device comprises a field-effect transistor having a source contact, a drain contact and a gate contact. The field-effect transistor may be, in particular, a p-type or an n-type transistor which is formed in the "front end" of a CMOS process.

Preferably, the dielectric layer is arranged at a metal electrode of the sensor device, which is electrically conductively connected to the gate contact of the field-effect transistor. The semiconductor structure is preferably a CMOS semiconductor structure. In particular, the metal electrode may be electrically conductively connected to the gate contact via an arrangement of metal and intermetal layers of the CMOS semiconductor structure. While the field-effect transistor of the CMOS semiconductor structure has been defined in the "front end", the arrangement of the metal electrode and the TiO$_2$ boundary layer is effected in the "back end", i.e. in a late process stage.

The sensor device of such a biochip accordingly has two series-connected capacitances which influence the coupling efficiency. Thus, the sensor device has a junction capacitance defined by the arrangement of electrolyte—TiO$_2$ boundary layer—metal electrode. The coupling efficiency is additionally influences by the gate capacitance of the MOSFET, which is determined by the arrangement of metal or polysilicon—SiO$_2$—semiconductor. A good coupling efficiency between biochip and electrolyte is achieved when the junction capacitance is as high as possible.

In the case of an embodiment of a biochip according to the invention that is constructed in a particularly simple manner, the dielectric TiO$_2$ boundary layer may constitute the gate oxide of the field-effect transistor. The gate oxide of the FET thus directly forms the dielectric boundary layer between electrolyte and semiconductor. The gate contact, which is otherwise composed of metal or polysilicon, is provided by the electrolyte in this case. Such a construction may be advantageous on account of its simple producibility as a "laboratory prototype biochip".

The dielectric layer preferably has a layer thickness of between 5 nm and 200 nm.

According to the invention, a method for producing a biochip, in particular a biochip according to the invention, for capacitive stimulation and/or detection of biological tissues comprises the following steps:
provision of a carrier structure;
formation of at least one stimulation and/or sensor device in or at the carrier structure;
arrangement of a dielectric layer at the stimulation and/or sensor device in such a way that one layer area of the dielectric layer is arranged at the stimulation and/or sensor device and the opposite layer area of the layer forms a stimulation and/or sensor area for capacitive stimulation and/or detection of biological tissues;
the dielectric layer comprising TiO$_2$.

Preferably, the step of arrangement of the dielectric layer comprises the sputtering of TiO$_2$. The sputtering of a metallic titanium target is preferably effected in an argon/oxygen mixture. The step of arrangement of the dielectric layer is preferably effected at the end (i.e. in the "back end" of a CMOS process.

BRIEF DESCRIPTION OF THE DRAWINGS

The invention is described by way of example below with reference to accompanying drawings of preferred embodiments, in which.

DETAILED DESCRIPTION OF THE PREFERRED MODE OF THE INVENTION

Figure 1:
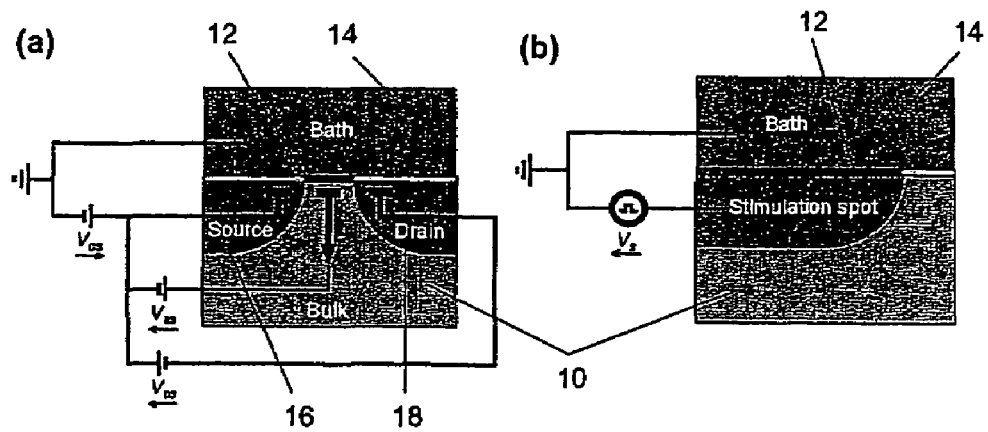
FIG. 1(a) shows an embodiment of a biochip according to the invention in a field-effect transistor circuitry as a potential sensor.
FIG. 1(b) shows a further embodiment of a biochip according to the invention in a stimulation circuitry.

FIG. 1(a) illustrates an embodiment of a biochip according to the invention in a field-effect transistor circuitry, which is used as potential sensor. The biochip has a patterned structure 10, which is a semiconductor structure. The substrate of the semiconductor structure 10 is electrically contact-connected by means of an ohmic contact and electrically connected to a voltage source $V_{BS}$. Arranged in the semiconductor structure 10 is a source contact 16 and also a drain contact 18 of a field-effect transistor, which are in each case electrically contact-connected. Arranged in the gate region of the field-effect transistor between the source contact 16 and the drain contact 18 is a dielectric layer having TiO$_2$, which separates the semiconductor structure 10 from the electrolyte or the bath 14. The dielectric layer 12 thus constitutes the gate oxide of the field-effect transistor.

Consequently, the embodiment illustrated in FIG. 1 is a "laboratory prototype biochip" having a particularly simple construction. A CMOS-compatible biochip according to the invention has a significantly more complex construction of the semiconductor structure 10. In particular, in the case of a CSMOS-compatible biochip, the gate oxide of the field-effect transistor (FET) is not formed by the dielectric TiO$_2$ boundary layer. Instead, the FET of a CMOS-compatible biochip has a conventional construction with a polysilicon gate contact and an SiO$_2$ gate oxide. In this case, the gate contact is connected to a metal electrode near the surface via an arrangement of metal and intermetal tracks, said metal electrode carrying the dielectric boundary layer made of $TiO_2$. However, in order to facilitate comprehension of the basic principle according to the invention, the rest of the description is given on the basis of a "laboratory prototype biochip".

That surface of the dielectric layer 12 which is remote from the semiconductor substrate 10, i.e. that interface which operationally makes contact with the electrolyte 14, constitutes a sensor area for capacitive detection of biological tissues or processes. To use a simplified mode of expression, in the case of a "laboratory prototype biochip", the conventionally metallic gate electrode of the field-effect transistor is replaced by the electrolyte. Consequently, charge transfers or electrical potential changes in the biological material which is situated near the dielectric layer 12 in the electrolyte 14 alter the electrical transport properties of the field-effect transistor by way of the field effect. In particular, the electrical conductivity between the source contact 16 and the drain contact 18 is influenced by such potential changes. This change in the channel conductivity of the field-effect transistor can be demonstrated in a customary manner. The dielectric layer 12 may also have a larger lateral extent than the channel region of the field-effect transistor.

FIG. 1(b) illustrates an embodiment of a biochip according to the invention in a stimulation circuit. A stimulation device, comprising for example a doped semiconductor region of the semiconductor structure 10 or a metal electrode, is electrically contact-connected, so that an external voltage signal can be applied relative to the electrical potential of the electrolyte. A dielectric layer 12 having $TiO_2$ is arranged between the stimulation device and the electrolyte 14. The interface of the dielectric layer 12 that is remote from the stimulation device constitutes a stimulation area for capacitive stimulation of biological tissues. This capacitive stimulation area, also referred to as stimulation spot, permits the capacitive excitation of biological material to be examined. The dielectric layer may also have a lateral extent beyond the stimulation device.

An embodiment variant of the production method according to the invention is illustrated below. The dielectric layer is applied on the stimulation and/or sensor device by means of a $TiO_2$ sputtering method. In this case, the $TiO_2$ layer is applied by sputtering from a metallic titanium target in an argon/oxygen mixture at 0.4 Pa and a distance of 60 mm. The sputtered titanium material reacts with the $O_2$ molecules in the gas space to form $TiO_2$. As an alternative to an RF sputtering method, it is also possible to use a sputtering method using a pulsed DC source having an equivalent DC power of 3 kW. The patterned silicon substrates (wafers) heated to about 400° C. rotate under the target so that the $TiO_2$ is applied at an average rate of 2 nm/min. For all of the wafers, a brief etching step in HF (so-called HF dip-etch) is carried out immediately prior to the production.

It has been shown that such $TiO_2$ layers withstand a 10 minute bath at 80° C. under ultrasonic influence in a cleaning solution that is sold under the brand name "Ticopur", without impairments of the interface properties being ascertainable. The surface layer of the dielectric layer is removed by less than 1 nm in this case.

In order to test the corrosion resistance, the biochips obtained were arranged in plastic Petri dishes ("Falcon 3001" type) that are often used in neurobiology, and were sterilized from both sides in each case for 30 minutes by UV irradiation in flow boxes.

The coating was effected using 2 ml of PBS (phosphate buffer saline) and 40 µl of collagen per dish, which, having been applied by pipetting, acted over night. The next day, the falcon dishes were rinsed once with ultrapure water (Millipore) and filled with a nutrient medium (13.89 g of DMEM, 3.7 g of $NaHCO_3$, 1 l of water at pH 6.8 (HCl or NaOH)). The medium was filtered in sterile fashion and added to it were 500 µl of L-glutamine, 5.5 ml of penicillin/streptomycin (antibiotics) and 100 ml of FCS (fetal calf serum).

The HEK cells cultivated in "Falcon 3001" Petri dishes were removed from a dish by pipetting, applied dropwise to the biochips in the nutrient medium in a ratio of 1:4 and stored in the incubator at 37° C. and 5% $CO_2$. Micrographs were recorded after 24, 36 and 72 hours in order to check the state of the cells and of the biochip.

All the cells, independently of the substrate, exhibited a similar cell division rate and acted in an uninfluenced manner in comparison with dielectric layers made of $SiO_2$. It can be inferred from this that, for all the materials examined, on the one hand no substances that adversely affected the cell culture were released, and on the other hand the morphology of the interface surface is suitable, in principle, for cell cultures.

Figure 2:
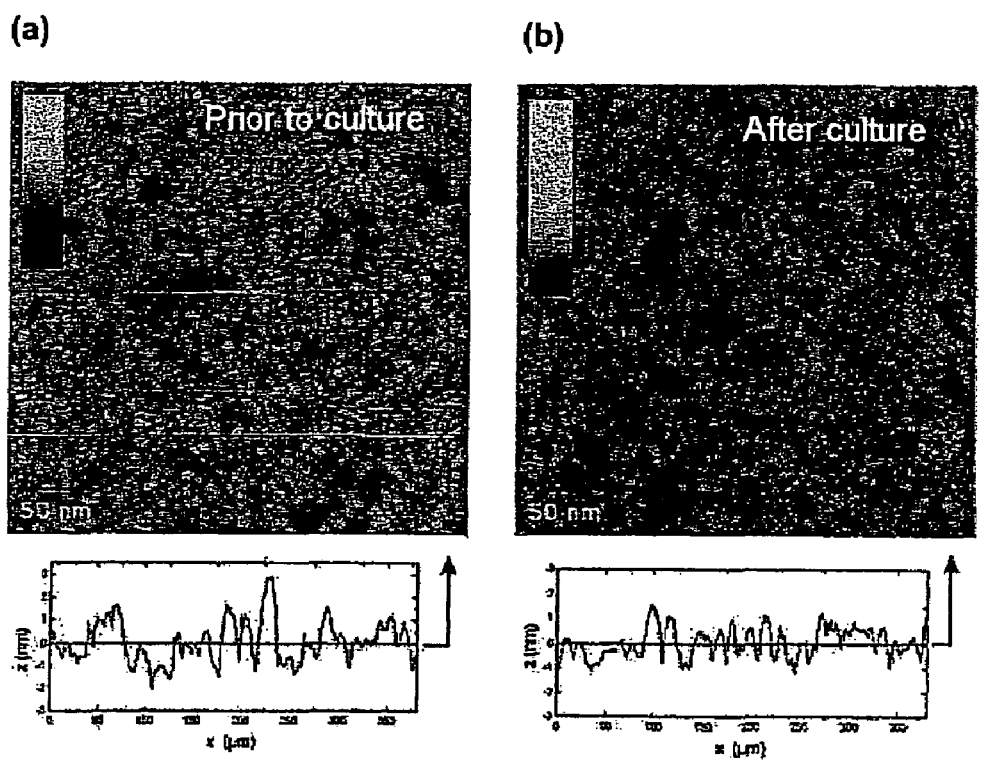
FIG. 2(a) shows a scanning force micrograph of a TiO$_2$ layer of an embodiment of a biochip according to the invention prior to contact with a biological material to be examined.
FIG. 2(b) shows a scanning force micrograph of the surface constitution and the surface profile of the TiO$_2$ layer from FIG. 2(a) after cultivation of fetal rat brain sections for 11 days.

FIG. 2(a) shows a force micrograph of both the surface constitution and the surface profile of a dielectric layer made of $TiO_2$ prior to being covered with biological material. FIG. 2(b) illustrates the surface constitution and the surface profile of the interface shown in FIG. 2(a) after cultivation of fetal rat brain sections for 11 days. The 11-day cell culture had no appreciable effects on the surface morphology. The entire surface exhibits height fluctuations in the nanometers range, as at the beginning of the experiment, and can thus be classified as smooth.

Figure 3:
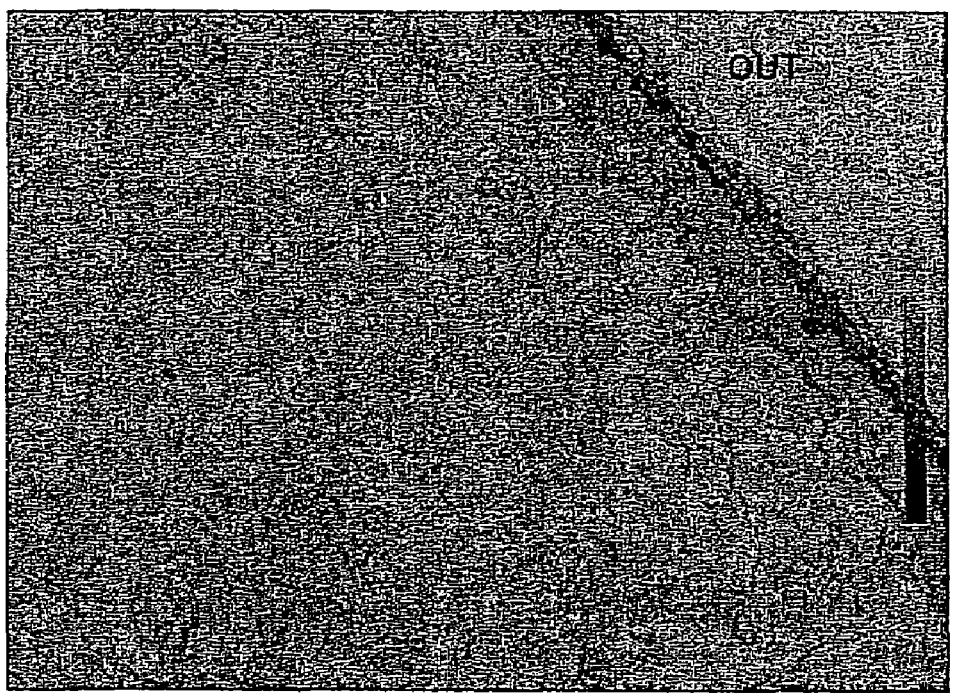
FIG. 3 shows a plan view of a dielectric layer made of TiO$_2$ of an embodiment of a biochip according to the invention, on which HEK cells that grow well are arranged.

FIG. 3 illustrates a biochip with a dielectric layer made of $TiO_2$ which is covered with a layer of HEK cells that grows well. It can be deduced from this that the dielectric $TiO_2$ layer is biocompatible since a successful growth of HEK (human embryonic kidney) cells could be achieved.

Figure 4:
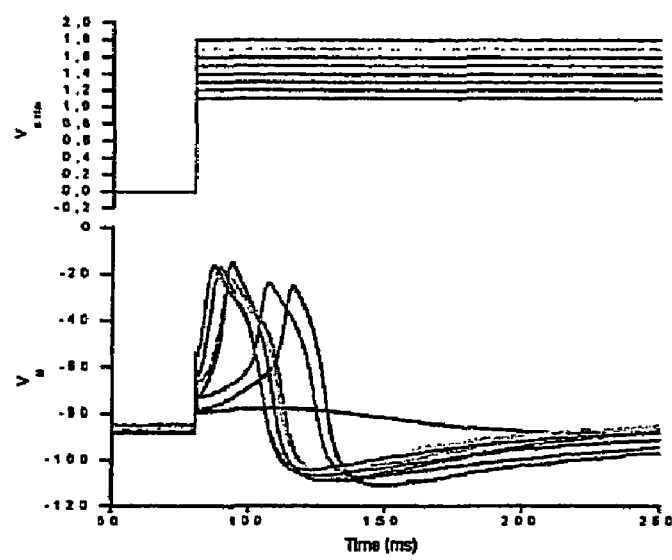
FIG. 4 shows a voltage-time diagram of a stimulation experiment on an isolated invertebrate cell using an embodiment of a biochip according to the invention.
Figure 5:
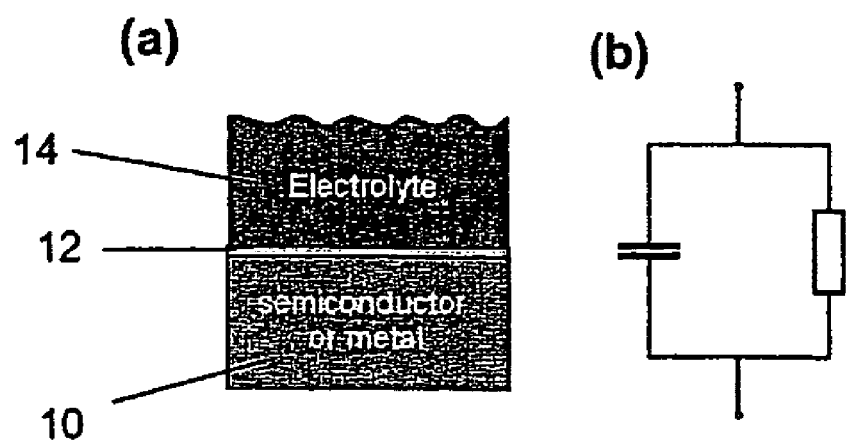
FIG. 5 shows a basic structure of the operational arrangement of a biochip relative to an electrolyte with the associated equivalent circuit diagram.

FIG. 4 illustrates a stimulation experiment with a further embodiment of a biochip according to the invention on an isolated invertebrate cell. Neurons of Lymnae stagnalis are stimulated capacitively with a stimulation device of the biochip by application of sudden changes of electrical voltage (upper diagram of FIG. 4) between the semiconductor structure lying below the neuron and the electrolyte. Via the capacitive dielectric/cell membrane voltage divider, a depolarizing voltage is momentarily dropped across the cell wall (lower diagram), which, above a specific threshold, triggers an action potential in the neuron. What is important is that this threshold, for the given thickness of the $TiO_2$ layer, is at approximately one volt and thus approximately at one third of the magnitude of corresponding dielectric layers made of $SiO_2$. The coupling efficiency of the dielectric layer made of $TiO_2$ to the biological material is thus significantly improved in comparison with conventional $SiO_2$ layers.

The invention claimed is:

1. A biochip for capacitive stimulation and/or detection of biological tissues, comprising:
   a carrier structure;
   at least one stimulation and/or sensor device, which is arranged in or at the carrier structure and comprises a metal electrode, an electrical potential of which can be controlled externally; and
   at least one dielectric layer, one layer area of which is arranged at the metal electrode and the opposite layer area of which forms a stimulation and/or sensor area for capacitive stimulation and/or detection of biological tissues, wherein the dielectric layer comprises $TiO_2$.

2. The biochip as claimed in claim 1, wherein the carrier structure comprises a semiconductor structure.

3. The biochip as claimed in claim 2, wherein the sensor device comprises a field-effect transistor having a source contact, a drain contact, and a gate contact.

4. The biochip as claimed in claim 3, wherein the dielectric layer is arranged at a metal electrode of the sensor device, and the metal electrode is electrically conductively connected to the gate contact of the field-effect transistor.

5. The biochip as claimed in claim 4, wherein the semiconductor structure is a CMOS semiconductor structure.

6. The biochip as claimed in claim 5, wherein the metal electrode is electrically conductively connected to the gate contact via an arrangement of metal and intermetal layers of the CMOS semiconductor structure.

7. The biochip as claimed in claim 2, wherein the dielectric layer forms a gate oxide of a field-effect transistor.

8. The biochip as claimed in claim 1, wherein the dielectric layer has a layer thickness of between 5 nm and 200 nm.

9. A method for producing a biochip for capacitive stimulation and/or detection of biological tissues, comprising:
   providing a carrier structure;
   forming at least one stimulation and/or sensor device in or at the carrier structure, wherein the at least one stimulation and/or sensor device comprises a metal electrode, an electrical potential of which can be controlled externally; and
   arranging a dielectric layer at the stimulation and/or sensor device in such a way that one layer area of the dielectric layer is arranged at the metal electrode and the opposite layer area of the layer forms a stimulation and/or sensor area for capacitive stimulation and/or detection of biological tissues, wherein the dielectric layer comprises $TiO_2$.

10. The method as claimed in claim 9, wherein the step of arranging the dielectric layer comprises sputtering $TiO_2$.

11. The method as claimed in claim 10, wherein the step of sputtering $TiO_2$ is effected in an argon/oxygen mixture.

12. The method as claimed in claim 9, wherein the arranging step comprises RF sputtering or sputtering via a pulsed DC source.

13. The method as claimed in claim 9, wherein the step of arranging the dielectric layer is effected as a back end process step of a CMOS process.

14. A biochip for capacitive detection of biological tissues, comprising:
   a carrier structure which comprises a semiconductor structure;
   at least one sensor device, which is arranged in or at the carrier structure, and comprises a field-effect transistor having a source contact, a drain contact, and a gate contact; and
   at least one dielectric layer, one layer area of which is arranged at a metal electrode of the sensor device and the opposite layer area of which forms a sensor area for detection of biological tissues, wherein the metal electrode is electrically conductively connected to the gate contact of the field-effect transistor, and wherein the dielectric layer comprises $TiO_2$.

* * * * *